(12) United States Patent
Michaelian

(10) Patent No.: US 8,353,700 B2
(45) Date of Patent: Jan. 15, 2013

(54) DENTAL DEVICE AND METHOD OF USE

(76) Inventor: Andre Michaelian, Las Vegas, NV (US)

( * ) Notice: Subject to any disclaimer, the term of this patent is extended or adjusted under 35 U.S.C. 154(b) by 461 days.

(21) Appl. No.: 12/779,679

(22) Filed: May 13, 2010

(65) Prior Publication Data

US 2011/0143309 A1    Jun. 16, 2011

(51) Int. Cl.
*A61C 17/24* (2006.01)
*A61C 1/18* (2006.01)

(52) U.S. Cl. ............ 433/82; 433/89; 433/112; 433/125; 222/104

(58) Field of Classification Search ............... 433/80–89, 433/112, 114, 125, 133; 401/154, 265; 222/63, 222/92, 95, 104, 107, 333; 464/19, 20
See application file for complete search history.

(56) References Cited

U.S. PATENT DOCUMENTS

| | | | |
|---|---|---|---|
| 2,400,912 A * | 5/1946 | Britt et al. | 433/82 |
| 2,738,528 A * | 3/1956 | Fridge, Sr. | 15/97.1 |
| 3,157,061 A | 11/1964 | Parker | |
| 3,232,076 A | 2/1966 | Sundt | |
| 3,389,468 A | 6/1968 | Lewis et al. | |
| 3,409,224 A | 11/1968 | Harp | |
| 3,472,045 A | 10/1969 | Nelsen | |
| 3,579,835 A | 5/1971 | Levenson | |
| 3,691,636 A * | 9/1972 | Deuschle | 433/82 |
| 3,747,367 A | 7/1973 | Muller | |
| 3,869,877 A | 3/1975 | Brahler | |
| 3,977,083 A * | 8/1976 | Leslie et al. | 433/82 |
| 4,124,316 A * | 11/1978 | O'Rourke | 401/184 |
| 4,266,933 A | 5/1981 | Warden et al. | |
| 4,417,874 A | 11/1983 | Andersson et al. | |
| 5,139,422 A * | 8/1992 | Straihammer et al. | 433/126 |
| 5,334,020 A | 8/1994 | Eckert | |
| 5,531,599 A | 7/1996 | Bailey | |
| 5,642,994 A * | 7/1997 | Chipian et al. | 433/82 |
| 5,692,901 A | 12/1997 | Roth et al. | |
| 5,871,353 A | 2/1999 | Pierce et al. | |
| 5,902,107 A | 5/1999 | Lowell | |
| 6,053,732 A | 4/2000 | Sale | |
| 6,099,309 A | 8/2000 | Cardarelli | |
| 6,257,886 B1 | 7/2001 | Warner | |
| 6,382,971 B1 * | 5/2002 | Randolph | 433/82 |

(Continued)

FOREIGN PATENT DOCUMENTS

GB      1 215 765 A      12/1970

*Primary Examiner* — Todd Manahan
*Assistant Examiner* — Michael R Ballinger
(74) *Attorney, Agent, or Firm* — Greenberg Traurig

(57) ABSTRACT

A prophy device incorporating a shaft and one or more corrugated members eliminates the need for plastic gears. The corrugated members effectively transfer rotational energy from a shaft to an applicator. In another version, a flexible paste chamber contains polish within a housing of the device. A difference between a rotational speed at a front of the paste chamber and rear of the chamber causes the flexible chamber to contract on itself thereby automatically forcing polish from the chamber and into a polish applicator. A rod extending through a paste chamber includes openings for contents to exit. The rod has one end in contact with a drive disk and a second end in contact with a front disk such that the ends of the rod are maintained substantially in place by the drive disk and front disk, respectively, but remain rotatably independent relative to the drive disk and front disk.

17 Claims, 6 Drawing Sheets

U.S. PATENT DOCUMENTS

| | | |
|---|---|---|
| 6,632,090 B1 | 10/2003 | Randolph |
| 6,875,017 B1 | 4/2005 | Tarr |
| 7,338,285 B1 * | 3/2008 | Balaban .................. 433/125 |
| 7,806,689 B2 * | 10/2010 | Lee et al. .................. 433/82 |
| 7,833,014 B2 * | 11/2010 | Michaelian .................. 433/125 |
| 2004/0014004 A1 | 1/2004 | Garrison et al. |
| 2006/0127844 A1 * | 6/2006 | Michaelian .................. 433/125 |
| 2009/0081610 A1 * | 3/2009 | Hayman et al. .................. 433/125 |

\* cited by examiner

DENTAL DEVICE AND METHOD OF USE

FIELD OF THE INVENTION

The embodiments of the present invention relate to dentistry. More particularly, the embodiments relate to a simple and inexpensive disposable tool for polishing teeth and automatically dispensing polishing paste.

BACKGROUND

Maintaining clean teeth is integral to having healthy oral environment. Accordingly, a myriad of products and dental services are available to clean teeth. More specifically, dental professionals offer cleaning and polishing services. Moreover, most experts recommend such services once or twice a year.

While the process of cleaning teeth utilizes one or more rigid tools for prying tarter and related build-up from the teeth, polishing paste is applied using an air or electric driven prophy device. Prophy devices conventionally communicate with an air or electric source which is driven by a motor. The prophy device may be disposable or may be sterilized after each polishing. In either case, the prophy device includes a polish applicator fabricated of a pliable material, such as rubber. In practice, a portion of polishing paste is manually placed in a small cup of the applicator. The applicator is then rotatably driven and placed in contact with the teeth to be polished. During a standard polishing, the polishing cup must be intermittently filled with polishing paste. Unfortunately, each filling of the polishing cup requires the dentist or hygienist to stop the polishing process. Thus, because of the numerous breaks, the time for polishing is unnecessarily extended.

In addition to wasting time, the refilling of the prophy cup requires the dentist to remove the instrument from the patient's mouth and refill the cup. This repeated removal of the instrument increases the risk of transferring a patient's saliva, food debris, or plaque and potential associated bloodborne pathogens.

Another disadvantage is that gears inside the current prophy devices tend to fail when used at high speed and/or for long durations. The failure increases both time and cost.

The patent literature is replete with apparatuses and devices integrating a source of polishing paste with the actual applicator. Accordingly, the dentist is not required to stop the polishing process to re-fill the cup. Nonetheless, each of the prior apparatuses and devices are impractical, complex and overly costly in relation to the conventional models discussed above. Thus, even though patented designs exist, they are not available in the market because of the noted shortcomings.

Conventional polishing devices also incorporate a system of plastic gears designed to rotate the polishing applicator. More specifically, a first plastic shaft attached at one end to a drive device extends an internal length of the prophy device where a gear resides at a second end of the shaft. A second shaft has a gear at a first end such that it meshes with the gear at the second end of the first shaft. The second shaft extends at an approximately 90° angle from the first shaft and is fixed at a second end to the polish applicator. Consequently, driving or rotating the first shaft causes the first shaft gear to transfer power (i.e., rotational energy) to the second gear which then drives or rotates the polish applicator for application of polish to the teeth. Unfortunately, the plastic gears tend to fail during use thereby requiring the operator to replace the prophy device. Not only is time wasted, but the cost to the care provider and patient increases.

Thus, there continues to be the need for a simple, inexpensive polishing device capable of automatically dispensing polish. In addition, the polishing device should eliminate the plastic gears which can fail when in operation.

SUMMARY

Accordingly, a first embodiment of the present invention comprises a disposable prophy device which contains and dispenses polishing paste. The paste is contained in a flexible paste chamber within a prophy housing. The unique design of the prophy angle allows the user to operate the prophy device at any speed without paste being dispensed as long as a prophy cup does not experience any resistance such as that created during contact with a tooth. As the prophy cup contacts a tooth, the resistance experienced by the cup is transferred to the paste chamber such that the paste chamber tends to contract around itself causing paste to be forced from the paste chamber and into the prophy cup. As more pressure is applied on the tooth, more paste is dispensed and when pressure is reduced, less of the paste is dispensed into the prophy cup. Therefore, the new prophy angle design delivers paste on demand in response to the level of pressure placed on the tooth by the prophy cup. It is common practice for the operator of a prophy angle to exert greater pressure on teeth that have significant plaque buildup than on teeth with little plaque buildup. In addition, the present invention allows desired function of the device regardless if the drive motor is operating in forward or reverse direction.

In one embodiment, a rod extending through the paste chamber includes one or more free ends such that said rod is partially or wholly independent of disks positioned on opposite ends of the past chamber.

In addition, the use of corrugated sections in combination with rigid shafts and disk members eliminates the gears of the prior art and provides for an ergonomic design. Even through there exists one or more bends in a housing of the prophy angle, the corrugated sections transfer rotational energy from a rotating shaft to a prophy cup without any gears.

During use a professional user (e.g., dental hygienist) removes an individually packaged prophy angle and inserts the drive end of the prophy device into the nose cone of a dental hand piece and when ready to use, a seal on the prophy cup is peeled off and the procedure may begin. The prophy device functions the same regardless if the drive motor is operating in forward or reverse direction. In another embodiment, a plug extending from the prophy cup seals the apparatus and is first pulled out to ready the apparatus for use. Herein, throughout the description of the embodiments of present invention, numerous references are made to paste. It should be understood that paste is intended to be construed broadly to cover any prophylaxis medium or dentifrice, such as paste or gel. In fact, the device herein is not limited to the dental industry and may facilitate non-dental applications of any type of paste, gel or materials having similar properties.

Other features, embodiments and variations will become evident from the following detailed description, drawings and claims.

DETAILED DESCRIPTION

It will be appreciated by those of ordinary skill in the art that the invention can be embodied in other specific forms without departing from the spirit or essential character thereof. The presently disclosed embodiments are therefore considered in all respects to be illustrative and not restrictive.

A disposable conventional prophy device is joined to an air or electric source and motor (i.e., hand piece motor) which drive a first shaft. The air or electric source is controlled by an operator through hand or feet movements. The first shaft then drives a second shaft via a pair of meshed gears. Then, the second shaft drives a polish applicator. As disclosed below, the embodiments of the present invention eliminate the need for gears and the repetitive manual application of polish into the prophy cup.

Figures 1, 2:
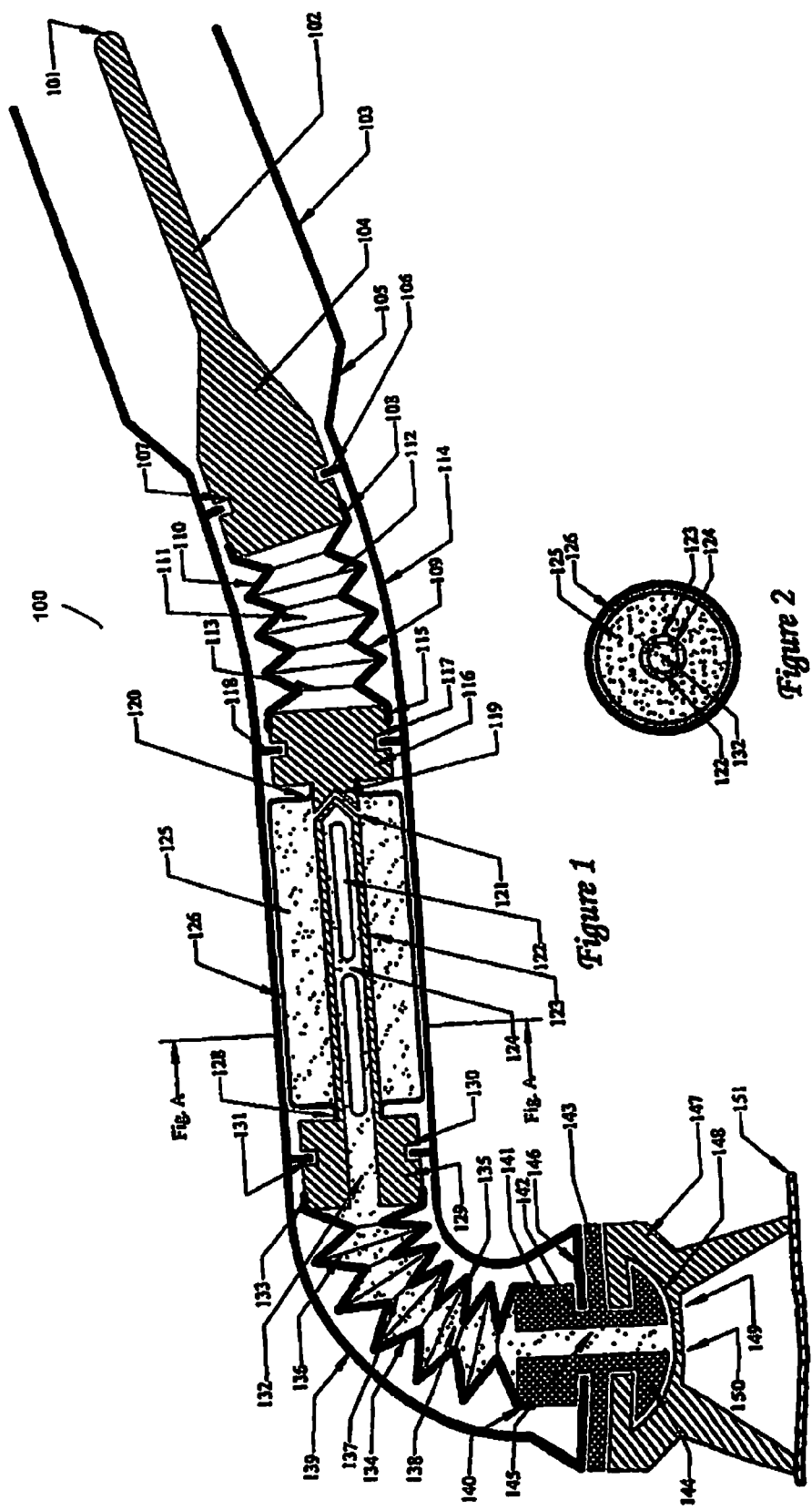
FIG. 1 shows an internal view of a first embodiment of the present invention.
FIG. 2 shows a cross-sectional view along direction A of FIG. 1.

Reference is now made to the figures wherein like parts are referred to by like numerals throughout. FIG. 1 shows a prophy device generally referred to by reference numeral 100. In a conventional manner, the prophy device 100 is received by a hand piece motor handle (not shown). A main housing 105 comprises a circular cross section, which incorporates a first bend 114, a second bend 139, a first open end 103 and a second open end 146. Within the main housing 105, there are multiple protrusions 106, 118, 131, and ends of open end 146 which act to maintain certain inner components in fixed positions while allowing the inner components to rotate about their longitudinal axes. The first open end 103 is sized to accept a standard nose cone of a dental hand piece motor and the second open end 146 accommodates placement of a prophy cup 147. In combination, the two bends 114, 139 provide an ergonomically designed device 100 for the user and also permit a wider range of access inside a patient's mouth.

The main housing 105 can be manufactured with different materials having different colors, textures and/or dimensions. It should be understood that the embodiments of the present invention are not intended to be limited to prophy paste and should be hereby construed to cover the application of any liquids, gels, pastes or similar materials.

A drive shaft 104 has a first rounded end 101 received by a nose cone of a hand piece motor and a second end 108 attached to a first corrugated drive 111. The hand piece motor maintains connection with the slender shaft 102 by means of a friction grip and transfers rotational energy from the hand piece motor to the drive shaft 104. The circular drive shaft 104 includes a slender shaft 102, widened body 104 and circular notch 107. The circular notch 107 receives protrusion 106 for maintaining the drive shaft 104 in place with respect to the main housing 105 and allowing free rotation of the drive shaft 104 about its longitudinal axis. The second end 108 of the drive shaft 104 is attached to the first corrugated drive 111 such that all the rotational energy generated by the hand piece motor is directly transferred to the first corrugated drive 111.

The first corrugated drive 111 is a hollow multi-fold member which transfers the rotational energy of the drive shaft 104 to a middle drive disk 116. The first corrugated drive 111 also facilitates transfer of the rotational energy through the first bend 114 of the main housing 105 between the drive shaft 104 and the middle drive disk 116. As the first corrugated dive 111 rotates about its longitudinal axis it forces the corrugated segments to contract on one side 110 and expand on the opposite side 109. This change in shape during rotation is possible because of the flexibility of the material used, the hollow nature of the design and the alternating wide 112 and narrow 113 circumferences forming the drive 111. By using this type of corrugated drive 111, the need for the gears of the prior art are eliminated. Prior art gear systems can fail and generate significant noise levels during use. Because of the unique design and function of the first corrugated drive 111 as described herein, the bend 114 between the axis of the drive shaft 104 and the axis of the middle drive disk 116 can be altered per final design requirements.

The circular middle drive disk 116 is attached to the first corrugated drive 111 at a first end 115 and a paste chamber 126 at a second end 120. The paste chamber 126 is fabricated a flexible material. The middle drive disk 116 also has a circular notch 117 which receives protrusion 118 for maintaining the middle drive disk 116 in place with respect to the main housing 105 and allowing free rotation of the middle drive disk 116 about its longitudinal axis. A concave portion 119 of the middle drive disk 116 extending into the paste chamber 126 accommodates a pointed end 121 of central rod 123. This accommodation permits the central rod 123 to rotate independently about its longitudinal axis while being prevented from diverging too substantially from a suitable position with respect to the middle drive disk 116.

The paste chamber 126 functions like a flexible reservoir wherein paste is stored and dispensed on demand during use. The paste chamber 126 attaches at a first end 120 to the middle drive disk 116 and a second end 128 to drive disk 129 which is hollow in the center and includes rod 123. Consequently, the rotational energy of the middle drive disk 116 is transferred to the drive disk 129 by the paste chamber 126 only. As long as there is no resistance placed on the drive disk 129, the paste chamber 126 is able to transfer the same rotational energy of the middle drive disk 116 to the drive disk 129 such that both rotate at the same speed. Since the chamber 126 is filled with paste 125, which has mass and occupies a certain volume, it functions like a solid segment in part due to centripetal forces pushing the paste against the walls of the paste chamber 126 when in operation. When resistance is placed on the drive disk 129, it creates a speed differential between the drive disk 129 and the middle drive disk 116 causing the paste chamber 126 to compensate for the speed differential by collapsing its flexible walls. As the chamber 126 turns on itself, the volume of the chamber 126 is decreased forcing the paste 125 within the chamber 126 to be pushed out through multiple openings 122 of the central rod 123. The greater the differential speed, the more paste 125 that is pushed out of the chamber 126 through openings 122. When the resistance on the drive disk 129 is removed, no further paste 125 is pushed out.

The circular drive disk 129 is held in place by protrusion 131 which is received by circular notch 130 on the drive disk 129. A first end 128 is attached to the paste chamber 126 and a second end 133 is attached to a second corrugated drive 138. The central rod 123 is an extension of the drive disk 129 with a pointed end 121 accommodated by the middle drive disk 116 and its concave portion 119. The central rod 123 has multiple openings 122 leading to a central channel 132 with one or more rigid support segments 124 for maintaining the shape of the rod 123 during use. As the paste chamber 126 begins collapsing the paste 125 within the chamber 126 is forced to pass through the openings 122 in the rod 123 into the central channel 132 which guides the paste 125 through the drive disk 129. The central rod 123 maintains a fixed distance between the middle drive disk 116 and the drive disk 129 preventing the collapsing paste chamber 126 from pulling the middle drive disks 116 and drive disk 129 toward one another during use. As the paste 125 within the chamber 126 is depleted, the flexible chamber 126 wraps completely around the central rod 123 with no further speed differential compensation.

FIG. 2 shows a cross-sectional view in the direction of A depicted in FIG. 1. The aspects, namely the channel 132, multiple openings 122 and rigid support segments 124, of the rod 123 are clearly visible in FIG. 2. During contraction of the chamber 126, paste 125 is forced from paste chamber 126 through openings 122 and into channel 132 where the paste 125 is forced through drive disk 129.

The second corrugated drive 138 functions like the first corrugated drive 111. The second corrugated drive 138 accepts paste 125 from the central channel 132 which leads through the central rod 123 and the drive disk 129. The second corrugated drive 138 is attached at a first end 133 to the drive disk 129 and at a second end 140 to a prophy cup holder 141. In this manner, the second corrugated drive 138 guides the paste 125 into a channel 145 of the prophy cup holder 141. The second corrugated drive 138 is a hollow multi-fold member which transfers the rotational energy of the drive disk 129 to the prophy cup holder 141. As the second corrugated drive 138 rotates about its curved longitudinal axis, it forces the corrugated segments to contract on one side 135 and expand on an opposite side 134. This change in shape during rotation is possible because of the flexibility of the material used, the hollow nature of the design and the alternating wide 136 and narrow 137 circumferences forming the drive 138. Using this type of corrugated drive 138 transfers rotational energy through bend 139 and eliminates the need for gears as used with prior art prophy designs. Because of the unique design of the second corrugated drive 138, paste 125 is forced and guided through the bend 139.

A circular notch 142 of the prophy cup holder 141 receives protrusion 146 maintaining prophy cup holder 141 in a fixed position during rotation about its longitudinal axis. Since the prophy cup holder 141 is attached to the second corrugated drive 138 which is attached to the drive disk 129, any rotational energy of the drive disk 129 is transferred to a button 144 of the prophy cup holder 141 with no loss in rotational speed. The prophy cup holder 141 defines a central channel 145 which allows paste 125 to be forced and guided from the second corrugated drive 138 into prophy cup 147. Beyond the second open end 146 of the housing 105, the prophy cup holder 141 incorporates a disk segment 143 which maintains the prophy cup holder 141 in place and prevents it from being pulled into the housing 105. Button 144 inserts into the prophy cup 147 to secure the cup 147.

The prophy cup 147 is a separate item which snaps into place on the button 144. The attachment is achieved via the flexible prophy cup 147 having an opening 148 for securely receiving the button 144. To achieve this attachment and prevent paste 125 from exiting therethrough, opening 148 of prophy cup 147 is slightly smaller in size than the receiving button 144 of the prophy cup holder 141. At an inside center of the prophy cup 147 a one way valve opening 149 allows extruding paste 125 to be forced through the prophy cup holder 141 and into the prophy cup 147 where it is used to clean the surface of teeth. The one way valve 149 prevents back flow of paste 125 and/or air from entering and traveling into the paste chamber 126. Ideally, the one way valve 149 is a circular flap which is greater in circumference than the channel 145 of the prophy cup 141. The one way valve 149 rotates about notch 150. Finally, the end of the prophy cup 147 is sealed by a removable film 151 to prevent drying of the paste 125 inside the device. It should be understood that the prophy cup 147 may include other designs and should be hereby construed to include different types of prophy items including prophy brushes and different shaped polishers.

Figure 3:
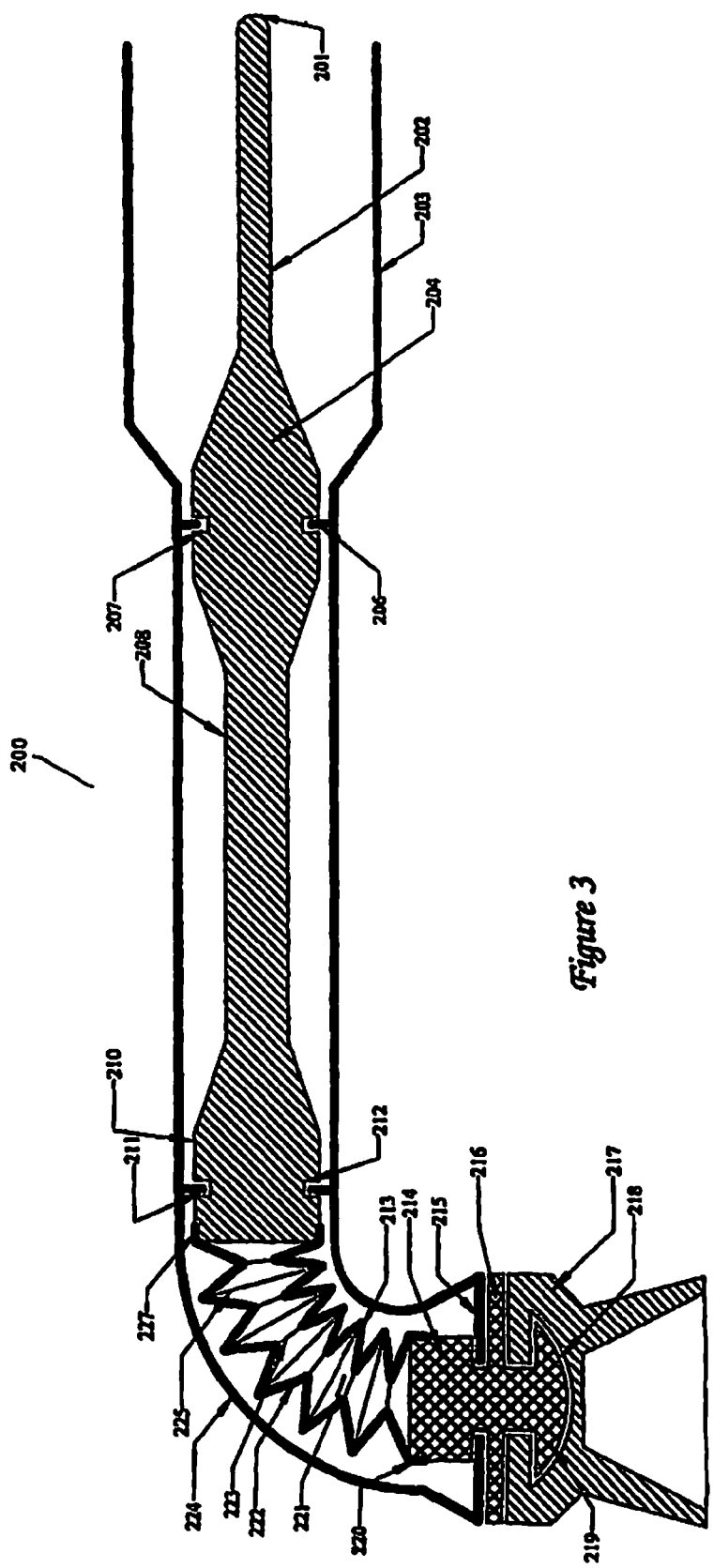
FIG. 3 shows an internal view of a second embodiment of the present invention.

FIG. 3 shows an alternative prophy design 200 without the first bend 114, first corrugated drive 111, middle drive disk 116, paste chamber 126, and drive disk 129. Additionally, prophy cup holder 141 does not contain a central channel. In this alternative design, a shaft 202 extends through a majority of the length of housing 203. A first end 201 of the shaft 202 is for attachment to a hand piece motor and a second end 227 attaches to a corrugated drive 221. The shaft 202 comprises a first expanded portion 204 having notch 207 for receipt of protrusion 206. As with the previous design, the protrusion 206 maintains the shaft 202 in place during rotation along its longitudinal axis. Similarly, and for the same purpose, a second expanded portion 210 has notch 212 for receipt of protrusion 211. Section 208 extends between the first expanded portion 204 and second expanded portion 210.

The corrugated drive 221 is a hollow multi-fold member which transfers the rotational energy of the shaft 202 to the prophy cup holder 214. As the corrugated drive 221 rotates about its curved longitudinal axis, it forces the corrugated segments to contract on one side 213 and expand on an opposite side 222. This change in shape during rotation is possible because of the flexibility of the material used, the hollow nature of the design and the alternating wide 225 and narrow 223 circumferences forming the corrugated drive 221. Using this type of corrugated drive 221 transfers rotational energy through bend 224 and eliminates the need for gears as used with prior art prophy designs.

A second end 220 of the corrugated drive 221 attaches to prophy cup holder 214. A disk 216 beyond the second end 215 of the housing 203 prevents the prophy cup holder 214 from being pulled into the housing 203. Like the embodiment of FIG. 1, a button 219 receives a flexible prophy cup 217. In this embodiment, only the prophy cup 217 contains paste loaded from a separate container by the operator for polishing teeth. For a new patient, a completely new prophy device is attached to the hand piece motor.

Figure 4:
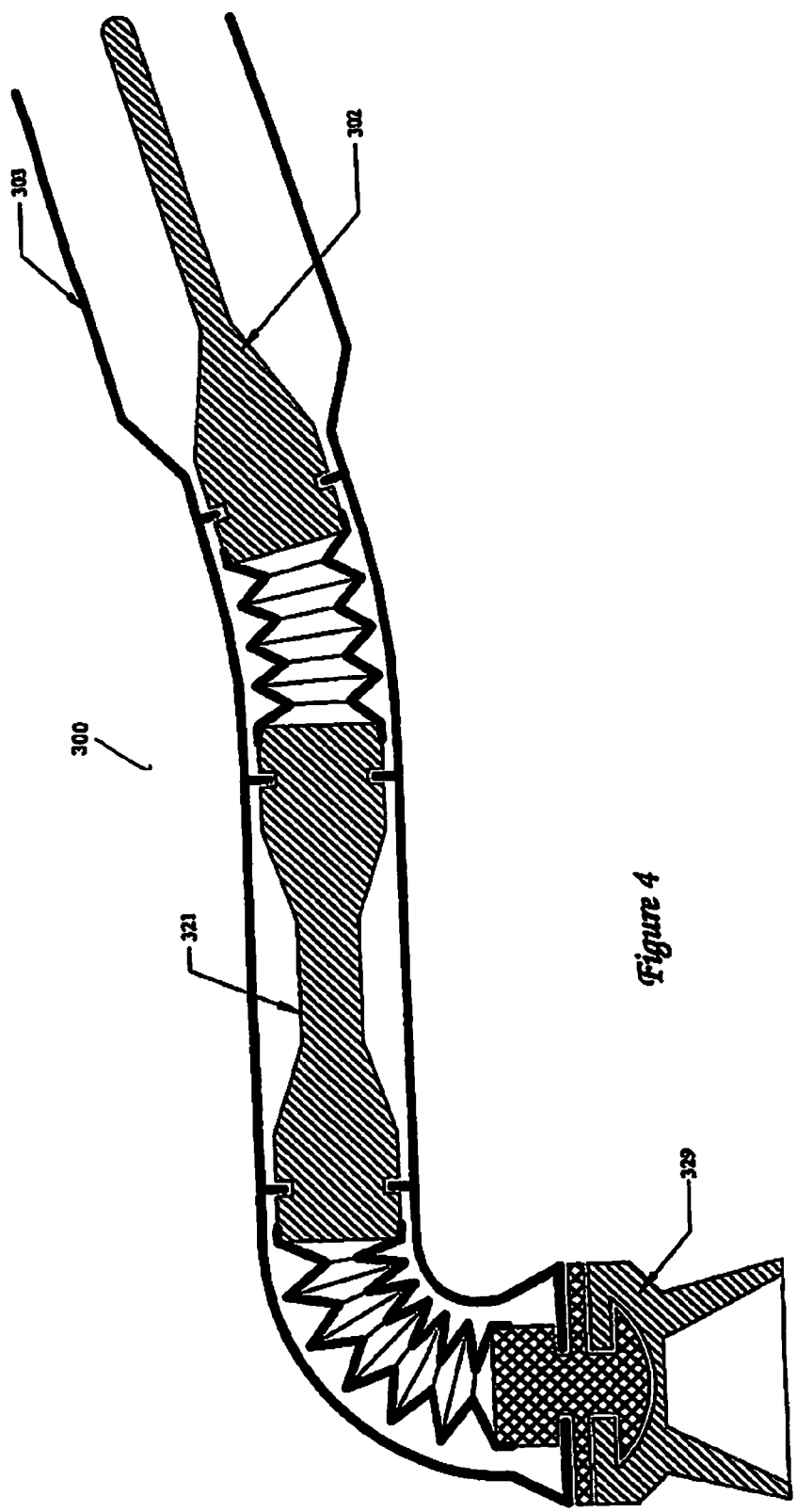
FIG. 4 shows an internal view of a third embodiment of the present invention.

FIG. 4 shows an alternative prophy design 300 without the ability to dispense prophy paste. This embodiment of a prophy device 300 comprising two rigid shafts 302 and 321 within housing 303. Rigid shaft 321 replaces the paste chamber 126 of the embodiment shown in FIG. 1. Like the embodiment shown in FIG. 3, the prophy cup 329 is manually loaded with prophy paste from a separate container by the operator.

Figure 5:
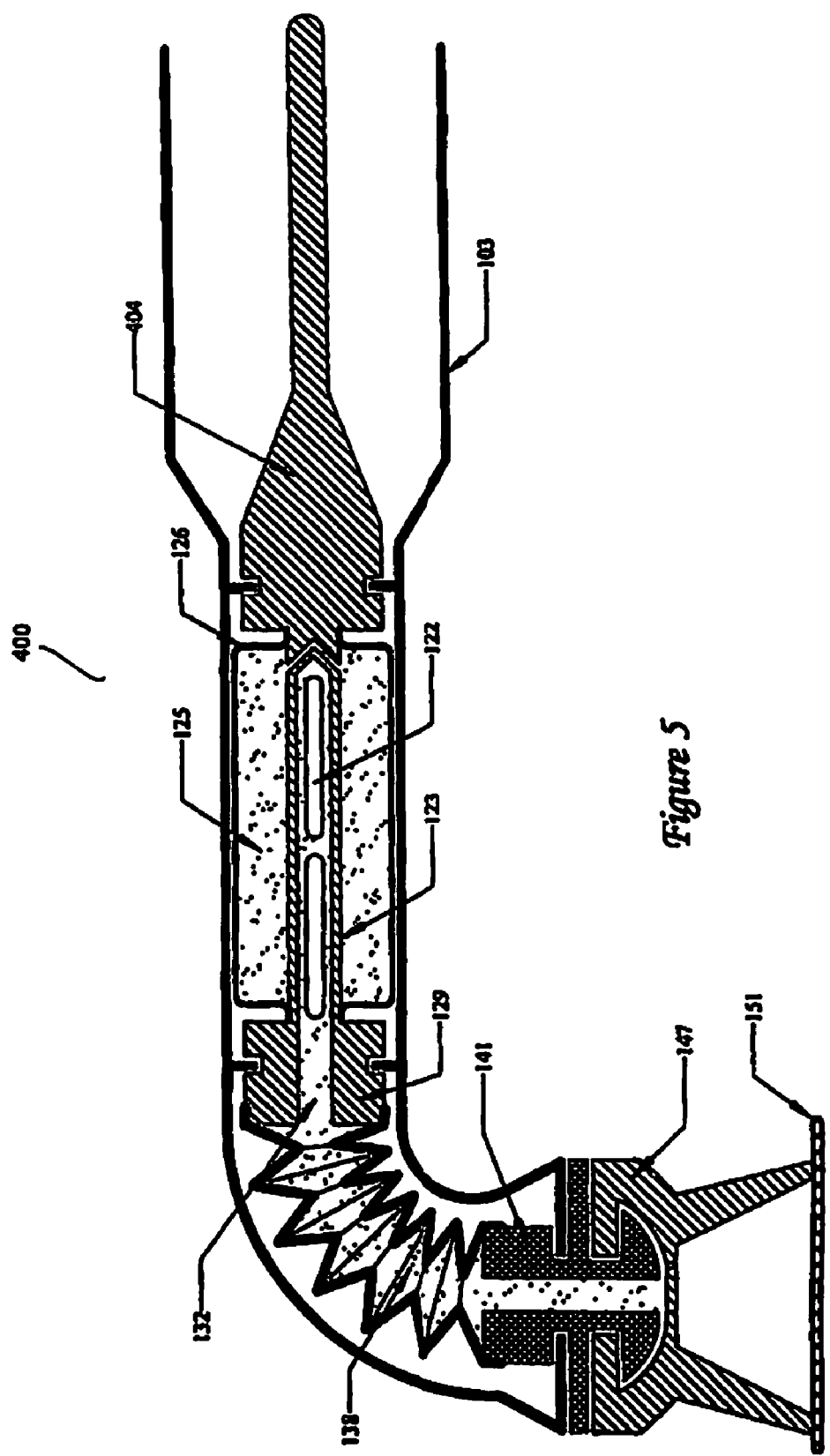
FIG. 5 shows an internal view of a fourth embodiment of the present invention.

FIG. 5 shows a fourth embodiment of a prophy device 400 similar to the embodiment shown in FIG. 1 without first corrugated drive 111, middle drive disk 116 and first bend 114. The first corrugated drive 111 and drive disk 116 is replaced with rigid shaft 404.

Figure 6:
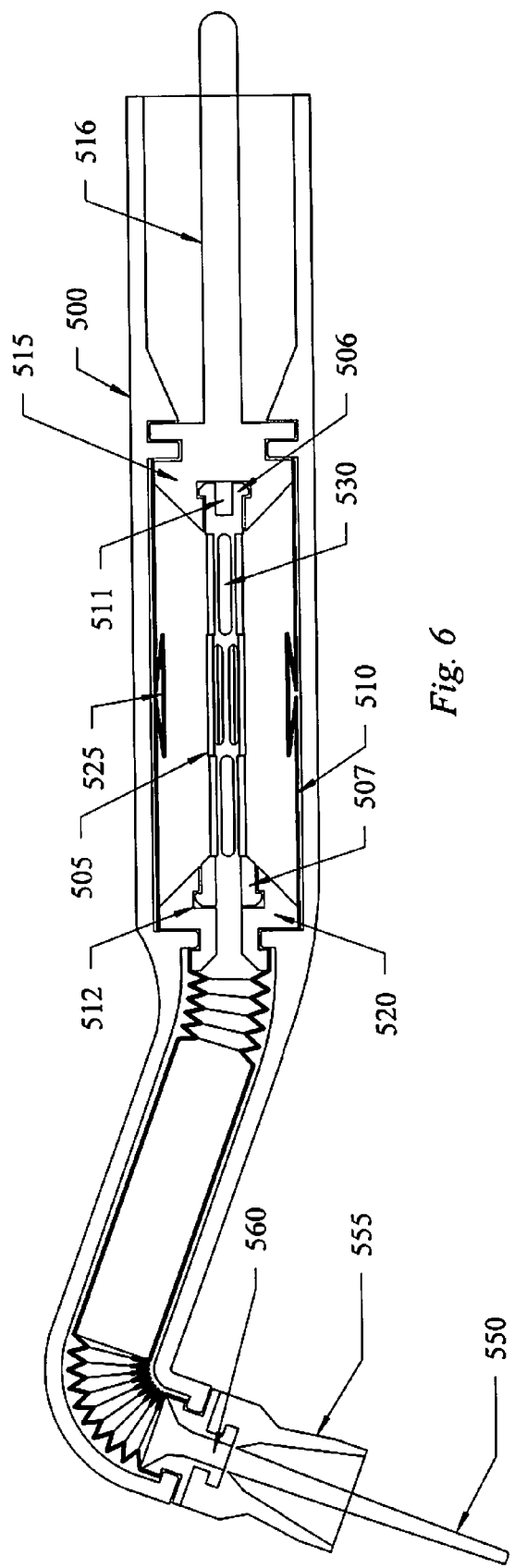
FIG. 6 shows an internal view of a fifth embodiment of the present invention prior to use.
Figure 7:
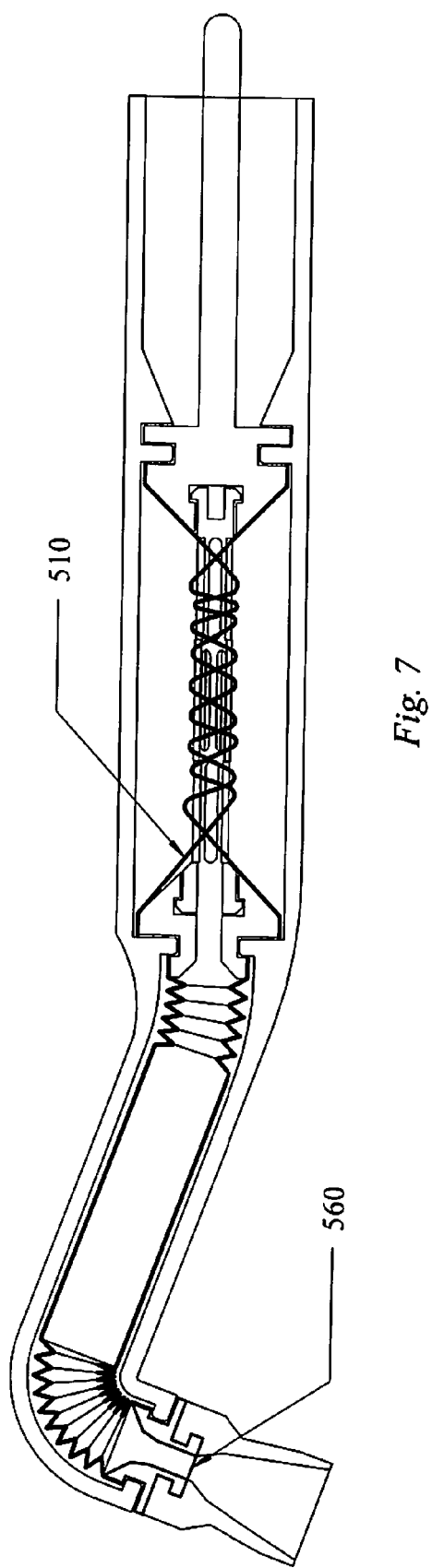
FIG. 7 shows an internal view of the fifth embodiment of the present invention after use.

FIGS. 6 and 7 show an alternative embodiment of the prophy device 500 having a rod 505 passing through the paste chamber 510 wherein the rod 505 is not rigidly fixed at either end 506, 507 thereof such that the rod 505 has freedom of flexibility on both ends 506, 507. The rod 505 prevents the drive disk 515, which is connected to or integral with the rotatable drive shaft 516, and front disk 520 from being pulled towards each other causing collapse on one another when the paste chamber 510 wraps around the central rod 505 during operation. As shown, ends 506, 507 of rod 505 clip or insert into corresponding cavities 511, 512 in the drive disk 515 and front disk 520, respectively. The cavities 511, 512 may take on any shape and size. Within the cavities 511, 512 the ends 506, 507 may contact the drive disk 515 and front disk 520 but remain rotationally independent of the drive disk 515 and front disk 520 such that rotation of the drive disk 515 and front disk 520 do not directly rotationally drive the rod 505. Depending on manufacturing tolerances, there may be some frictional rotation of the rod 505 caused by intermittent contact with the drive disk 515 and front disk 520 but the speed of rotation of the rod 505 is not intended to match the other rotating components. In other embodiments, the rod 505 is maintained in position with concave portions of the disk members like that shown in FIG. 1 such that the disk members 515, 520 accommodate pointed ends of the rod. This accommodation permits the rod to, once again, remain independent about its longitudinal axis while being prevented from diverging too substantially from a suitable position with respect to the disk members 515, 520.

The paste chamber 510 includes additional, flexible material 525 allowing the paste chamber 510 to wrap around the rod 505 effectively forcing the paste from the paste chamber 510 via openings 530. The extra material 525 also prevents the tension, caused by the shrinking paste chamber 510, from tearing the paste chamber 510. FIG. 6 shows the paste chamber 510 prior to use with the paste chamber 510 full or material (e.g., paste). FIG. 7 shows the paste chamber 510 after use with the paste chamber 510 substantially empty and wrapped around the rod 505.

FIG. 6 also shows a plug 550 extending from a front portion of the prophy apparatus 500. The plug 550 extends from boundaries defined by prophy cup device 555 making the plug 550 accessible to users. A first end of the plug 550 is configured to seal or cover opening 560 near a paste exit into the prophy cup device 555. Prior to use the plug 550 keeps the paste from drying out or otherwise being effected by the environment external to the prophy apparatus 500. When ready to use, the plug 550 is removed allowing the paste to exit once the device is activated. In the current embodiment, the plug 550 is an extension and part of the cup device 555 such that when ready to use the operator pulls the plug 550 with sufficient force severing plug 550 at its narrowest point near opening 560 exposing opening 560 to allow paste to pass through cup device 555. In other embodiments, the plug 555 may be held in place using adhesives or may fit over the opening 560.

The prophy device designs described herein solve the problems, namely complexity, cost of manufacture and failure, associated with the prior art devices. Consequently, the instant designs are able to functionally compete with current commercial models at less cost. Dentists and consumers will both benefit from the unique uncomplicated design.

It should be understood that materials besides dental paste may be applied to items in fields of use unrelated to the dental industry.

Although the invention has been described in detail with reference to several embodiments, additional variations and modifications exist within the scope and spirit of the invention as described and defined in the following claims.

I claim:
1. An application device comprising:
a housing;
a rotatable drive shaft having a first end for attachment to a drive means;
a front disk;
a paste chamber connecting said rotatable drive shaft to said front disk and positioned to transfer rotational energy from said rotatable drive shaft to said front disk;
a rod positioned within said paste chamber and extending between a drive disk to said front disk, said rod having one or more openings providing means for paste to exit said paste chamber, said rod further having a first end maintained by a drive disk and a second end maintained by said front disk such that said first and second ends of said rod are maintained substantially in place by said drive disk and front disk, respectively, but are rotatably independent relative to said drive disk and front disk; and
an applicator positioned on a front end of said application device.

2. The applicator device of claim 1 wherein said paste chamber is configured to wrap around said rod as contents exit.

3. The application device of claim 1 further comprising one or more corrugated members.

4. The application device of claim 1 wherein said first end of said rod is maintained by said drive disk by inserting said first end of said rod into a cavity in the drive disk, said cavity configured to allow said first end of said rod to rotate independent of said drive disk.

5. The application device of claim 1 wherein said second end of said rod is maintained by said front disk by inserting said second end of said rod into a cavity in the front disk, said cavity configured to allow said second end of said rod to rotate independent of said front disk.

6. An application device comprising:
a housing;
a rotatable drive shaft having a first end for attachment to a drive means and a second end, in the form of a drive disk, attached to a rear portion of a flexible paste chamber;
a front disk member attached to a front portion of said paste chamber, said paste chamber configured to transfer rotational energy from said rotatable drive shaft to said front disk;
a rod positioned within said paste chamber and extending between said drive disk to said front disk, said rod having one or more openings providing means for paste to exit said paste chamber, said rod further having a first end in contact with said drive disk and a second end in contact with said front disk such that said first and second end are maintained substantially in place by said drive disk and front disk, respectively, but being rotatably independent relative to said drive disk and front disk; and
an applicator positioned on a front end of said application device.

7. The applicator device of claim 6 wherein said paste chamber is configured to wrap around said rod as contents exit.

8. The application device of claim 6 further comprising one or more corrugated members.

9. The application device of claim 6 wherein said first end of said rod contacts said rotatable drive shaft by inserting said first end of said rod into a cavity in the drive disk, said cavity configured to allow said first end of said rod to rotate independent of said drive disk.

10. The application device of claim 6 wherein said second end of said rod contacts said front disk by inserting said second end of said rod into a cavity in the front disk, said cavity configured to allow said second end of said rod to rotate independent of said front disk.

11. The application device of claim 6 wherein said applicator has a plug extending therefrom, said plug configured to maintain contents of said paste chamber in an appropriate state.

12. An application device comprising:
   a housing;
   a rotatable drive shaft having a first end for attachment to a drive means;
   a front disk;
   a paste chamber positioned to transfer rotational energy from said rotatable drive shaft to said front disk;
   a rod positioned within said paste chamber and extending between a drive disk to said front disk, said rod having one or more openings providing means for paste to exit said paste chamber wherein a first end of said rod is in contact with said drive disk and a second end of said rod is in contact with said front disk such that said first and second ends of said rod are maintained substantially in place by said drive disk and front disk, respectively, but are rotatably independent relative to said drive and front disk; and
   an applicator positioned on a front end of said application device, said applicator having a plug extending therefrom, said plug configured to maintain contents of said paste chamber in an appropriate state.

13. The application device of claim 12 wherein said applicator is a prophy cup.

14. The applicator device of claim 12 wherein said paste chamber is configured to wrap around said rod as contents exit.

15. The application device of claim 12 further comprising one or more corrugated members.

16. The application device of claim 12 wherein said first end of said rod contacts said drive disk by inserting said first end of said rod into a cavity in the drive disk, said cavity configured to allow said first end of said rod to rotate independent of said rotatable drive disk.

17. The application device of claim 12 wherein said second end of said rod contacts said front disk by inserting said second end of said rod into a cavity in the front disk, said cavity configured to allow said second end of said rod to rotate independent of said front disk.

* * * * *